United States Patent [19]

Bryant, III

[11] Patent Number: 4,667,037

[45] Date of Patent: May 19, 1987

[54] DEALKYLATION OF OPIOID ETHERS

[75] Inventor: Walter M. Bryant, III, Elkton, Md.

[73] Assignee: E. I. Du Pont de Nemours and Company, Wilmington, Del.

[21] Appl. No.: 742,069

[22] Filed: Jun. 6, 1985

[51] Int. Cl.$^4$ ............... C07D 489/02; C07D 489/06; C07C 37/055

[52] U.S. Cl. ........................ 546/44; 546/45; 546/46; 546/74; 568/805

[58] Field of Search ............ 568/805; 546/44, 45, 546/46, 74

[56] References Cited

U.S. PATENT DOCUMENTS

| | | | |
|---|---|---|---|
| 2,697,732 | 12/1954 | Mavity | 568/805 |
| 2,806,033 | 9/1957 | Lewenstein et al. | 546/45 |
| 4,232,028 | 11/1980 | Razdan et al. | 546/45 X |
| 4,351,968 | 9/1982 | Harris | 568/805 X |

FOREIGN PATENT DOCUMENTS 913077 10/1972 Canada .

OTHER PUBLICATIONS

M. V. Bhatt and S. U. Kulkarni, Synthesis, 249 282 (1983).

Primary Examiner—Donald G. Daus
Assistant Examiner—Diana G. Rivers

[57] ABSTRACT

An improved process for the dealkylation of alkyl aryl ethers to aryl phenols is provided. In this process, an alkyl aryl ether, such as a methyl ether of an opioid, is contacted with an aqueous acid selected from HBr, HCl, or HI which contains at least one equivalent weight, based on the ether, of boric acid or an inorganic salt of a metal selected from Li, Na, K, Al, Mg, Ca, Mn and Ni. $MgBr_2$ in aqueous HBr is preferred in dealkylating an N-substituted 14-hydroxydihydronorcodeine.

10 Claims, No Drawings

DEALKYLATION OF OPIOID ETHERS

BACKGROUND OF THE INVENTION

1. Field of Invention:

This invention relates to processes for the dealkylation of alkyl aryl ethers to aryl phenols and more particularly to such processes using inorganic acids containing selected accelerators.

2. Prior Art:

A variety of reagents have been used to dealkylate alkyl aryl ethers. Commonly used reagents include hydrobromic acid, boron tribromide, organic mercaptides, and trimethylsilyl halides. The cleavage of ethers has recently been reviewed [M. V. Bhatt and S. U. Kulkarni, Synthesis, 249 (1983)].

While these standard methods of dealkylation have proven acceptable for a variety of simple ethers, the rate of dealkylation of more complicated ethers is often sufficiently slow that rather harsh reaction conditions or long reaction times are necessary to effect complete dealkylation, resulting in extensive decomposition and hence lower yield of the desired dealkylated product.

Canadian Pat. No. 913077 issued on Oct. 24, 1972 to Endo Laboratories, Inc., discloses the preparation of a variety of N-substituted 14-hydroxydihydronormorphines by dealkylation of the corresponding 3-methyl ethers. This dealkylation is exemplified by reaction with pyridine hydrochloride at 190°–195° C. for 75 minutes. No yield is given for this dealkylation. Other dealkylation reagents include hydrogen chloride, hydrogen chloride in acetic acid, hydrogen chloride in the presence of zinc chloride, ferric chloride, or antimony trichloride, hydrogen bromide, hydrogen bromide in acetic acid, hydrogen iodide, etc.

The need exists for a method of accelerating the cleavage of alkyl aryl ethers which react only sluggishly under simple acidic conditions without increasing the temperature or time of the reaction sufficiently to result in extensive decomposition.

SUMMARY OF THE INVENTION

According to the present invention there is provided in the process of dealkylating an alkyl aryl ether by contacting the ether with an aqueous acid selected from HBr, HCl, or HI, the improvement comprising: contacting an alkyl aryl ether with the aqueous acid containing at least one equivalent weight, based on the ether, of boric acid or an inorganic salt of a metal selected from Li, Na, K, Mg, Al, Ca, Mn and Ni.

In a preferred process, addition of an equivalent or more of a halide salt of lithium, magnesium, sodium, potassium, or calcium to the acidic dealkylation medium results in a rate enhancement of four to five times the rate in the absence of the salt. Aluminum results in the same level of rate enhancement; however, aluminum is not preferred due to the toxicity of any residual aluminum which may be present in the product.

DETAILED DESCRIPTION OF THE INVENTION

The process of the present invention surprisingly provides a convenient means to greatly accelerate the acidic dealkylation of alkyl aryl ethers which otherwise are only slowly dealkylated under normal acidic conditions. The alkyl group is usually lower alkyl, i.e., 1–4 carbon atoms, and is generally a methyl group. In general, the aryl moiety of the ethers will also contain a basic nitrogen which contributes to the decrease in the rate of the dealkylation. In particular, this process is especially effective for the dealkylation of opioid ethers, specifically N-substituted 14-hydroxydihydronorcodeines. The N-substituent is preferably cyclobutylmethyl.

The ethers are all readily available commercially or using literature methods to prepare them.

The acidic conditions used to dealkylate the ethers are aqueous solutions of hydrogen halides, specifically, hydrochloric acid, hydrobromic acid, or hydroiodic acid. Hydrobromic acid is preferred at an HBr concentration up to about 48% by weight, preferably in the range of about 28%–48% by weight.

In general, the inorganic salt which is added will be a halide salt where the halide is the same as that in the hydrogen halide being used, although hybrid systems such as hydrogen chloride/magnesium bromide or hydrogen chloride/lithium bromide can be used. In addition to the inorganic halide salts, the addition of boric acid is found to result in a five-fold rate enhancement. At least one equivalent weight of boric acid or the salt is used based on the weight of the ether. The useful inorganic salts are those of lithium, sodium, magnesium, aluminum, potassium, calcium, manganese, and nickel. The preferred salts are the bromide salts of lithium, sodium, magnesium, potassium or calcium. Magnesium bromide is most preferred.

The dealkylation reaction is conducted at the reflux temperature of the mixture, and this temperature will of course be dependent upon the exact composition of the particular mixture, but will generally be beween 100° and 130° C.

Constant boiling 48% aqueous hydrogen bromide is a classic demethylating agent for alkaloids. When 48% by weight hydrogen bromide at reflux is used in an attempt to demethylate N-cyclobutylmethyl-14-hydroxydihydronorcodeine, extensive decomposition is observed. To avoid this decomposition, it is necessary to use more dilute solutions of hydrogen bromide (about 28% by weight aqueous hydrogen bromide). The more dilute conditions result in a lowering of the reflux temperature of the mixture from about 125° C. for constant boiling 48% hydrogen bromide to about 110° C. for 28% aqueous hydrogen bromide. The lower reaction temperature in combination with the lower concentration of hydrogen bromide results in extended reaction times requiring 20 to 24 hours for the demethylation to go to 97% completion.

The addition of one equivalent of magnesium bromide is found to result in a dramatic increase in the rate of this demethylation. After six hours at reflux (110° C.), the demethylation reaction is complete without giving rise to the decomposition observed with 48% aqueous hydrogen bromide. The demethylation reaction is thus about four times faster in the presence of the magnesium bromide.

The effect of addition of a variety of inorganic bromides to the aqueous hydrogen bromide demethylation of N-cyclobutylmethyl-14-hydroxydihydronorcodeine was determined. Table I illustrates the effect of these additions on the rate of the demethylation.

Rate enhancement can also be achieved by the addition of boric acid. The addition of one equivalent of boric acid to the hydrogen bromide demethylation medium resulted in about a five-fold increase in the rate of the reaction, equivalent to that observed when lithium bromide is added.

A similar acceleration was observed when salts were added to the demethylation reaction conducted in aqueous hydrogen chloride. When N-cyclobutylmethyl-14-hydroxydihydronorcodeine was treated with constant boiling hydrochloric acid ($\approx 20\%$ by weight hydrogen chloride) at reflux $\approx 90\%$ demethylation was observed after 68 hours. Since the reaction was shown to be first order in N-cyclobutylmethyl-14-hydroxydihydronorcodeine, extrapolation to 97% conversion results in a reaction time of $\approx 100$ hours. Addition of three equivalents of magnesium chloride resulted in optimal rate enhancement with reaction now requiring 26 hours to go to 95% completion. The addition of magnesium chloride to the hydrogen chloride demethylation thus also resulted in a four-fold increase in the rate.

Several hybrid systems were also examined. Addition of magnesium bromide to the aqueous hydrogen chloride demethylation medium resulted in about a five-fold rate enhancement, the reaction now requiring 20 hours to go to 98% completion. Addition of lithium bromide to the aqueous hydrogen chloride demethylation resulted in a similar rate enhancement. Even greater rate enhancement was observed when both magnesium chloride and ammonium iodide were added to the aqueous hydrogen chloride demethylation with 97% of the starting material being consumed in 8 hours, however, the presence of the iodide resulted in additional by-products being formed and consequently unacceptably low product purity.

As is readily apparent, the choice of the accelerator used to accelerate a particular dealkylation will be dependent upon a number of considerations. Included among these considerations will be the cost of the inorganic additive, the potential consequences of trace amounts of residual inorganic in the final product, the amount of rate enhancement necessary to make the dealkylation commercially feasible, and the ease of handling the particular reaction mixture. Several inorganic accelerators which are generally preferred are magnesium bromide, boric acid, lithium bromide, and sodium bromide.

The details of this invention can be further understood by the following examples in which percentages are by weight and temperatures are in degrees centigrade. The examples illustrate the procedure used to establish the rate enhancements of various inorganic salts and boric acid.

CONTROL EXAMPLE

Rate Accelerator Not Adddded

To a 100 ml round bottom flask equipped with a condenser and a nitrogen purge was charged N-cyclobutylmethyl-14-hydroxydihydronorcodeine (6.3 g, 17 mmoles), 48% aqueous hydrobromic acid, (19.7 g 13.2 ml) and 8.9 ml of deionized water. With good agitation, the reaction was heated to 109° and refluxed gently at 109±1° for 22-24 hours to yield a tan slurry, at which point then layer chromatography indicated 97-98% conversion. The reaction mixture was added to 200 ml of boiling water and the mixture was refluxed for 1 hour until a homogeneous yellow solution was obtained. Activated charcoal (1.0 g) was added and the mixture was heated at reflux for 10 minutes. The charcoal was removed by hot filtration to give a colorless solution.

The solution was cooled to 90±2° and the pH was adjusted to 9 with 28% NH$_4$OH. The mixture was then stirred at 0°-5° for 1 hour. The precipitate was filtered off, washed with cold water (3×10 ml), dried overnight in a vacuum oven to yield N-cyclobutylmethyl-14-hydroxydihydronormorphine free base (4.6 g, 75.9%).

The free base was dissolved in 53 ml of tetrahydrofuran containing 4% water in a 100 ml round bottom flask equipped with a condenser and a nitrogen purge. The solution was heated to 50°, and then the pH was adjusted to 3 by the addition of 36% aqueous hydrochloric acid (3.0 ml) over a ten minute period. The mixture was cooled to 0°-5° and then was stirred for 1-2 hours. The resulting precipitate was filtered off and washed with tetrahydrofuran (2×10 ml, containing 4% water). The product was dried overnight in a vacuum oven at 90°-100° to give 4.5 g (67.4%) of N-cyclobutylmethyl-14-hydroxy dihydronormorphine hydrochloride, m.p. 274°-275°.

EXAMPLE 1

MgBr$_2$ as Demethylation Rate Enhancer

To 144 ml of deionized water in a 5 liter round-bottomed flask equipped with a condenser and a nitrogen purge was added 1079 g of 48% aqueous hydrogen bromide. Magnesium bromide hexahydrate (468 g; 1.6 moles) was added over 30 minutes and the mixture was stirred until all the magnesium bromide had dissolved. N-cyclobutylmethyl-4-hydroxydihydronorcodeine (606 g; 1.6 moles) was added over 30 minutes. The resulting slurry was heated to reflux (108°) over a 30 to 60 minute period during which time the starting material dissolved. The mixture was stirred at reflux for 6 hours, during which time the product began to separate. Thin layer chromatography indicated approximately 97-98% conversion. The resulting slurry was cooled to 25° to 30° over a 2 to 3 hour period and the product was collected by filtration.

The product was worked-up as follows: The filter cake was dispersed in methanol (4.0 liters) and the mixture was heated to reflux to dissolve the product. Activated charcoal (8 g) was added and the reflux was continued 15 minutes. The charcoal was removed by hot filtration. The pH of the warm (50° to 60°) filtrate was adjusted to 9 by addition of 28% aqueous ammonia (236 ml) and 2.0 liters of water was added. The resulting slurry was cooled to 5° over a 2 hour period and the product was collected by filtration and washed with 4.0 liters of ice water. This product was added to 3200 ml of tetrahydrofuran under nitrogen and 320 ml of water was added to completely dissolve the product. Activated charcoal (8 g) was added and the mixture was heated to reflux and stirred at reflux for 30 minutes. The charcoal was removed by hot filtration and the temperature of the filtrate was adjusted to $\approx 50°$. The pH of the filtrate was adjusted to 3 by addition of 37% aqueous hydrogen chloride (141 ml) over a 45 minute period. The resulting slurry was cooled to 5° over a 2 hour period and then was stirred at 5° for one hour. The product was collected by filtration and washed with 1600 ml of tetrahydrofuran. The product was dried in a vacuum oven at 110° for 24 hours to give 484.6 g (76.5%) N-cyclobutylmethyl-14-hydroxydihydronormorphine hydrochloride, m.p. 277°-278°.

EXAMPLE 2

Lithium Bromide As Demethylation Rate Enhancer

To a 100 ml round bottom flask equipped with a condenser and nitrogen purge was charged N-cyclobutylmethyl-14-hydroxydihydronorcodeine (7.6 g, 20 mmoles), lithium bromide (1.8 g, 20 mmoles), 48% aqueous hydrobromic acid (16.6 g, 100 mmoles) and 3.7 g of deionized water. The resulting mixture was heated to 103° and refluxed at 103±2° for 5 hours, during which time a lavender slurry resulted. Thin layer chromatography indicated approximately 97–98% conversion. The resulting slurry was cooled to 25° and was allowed to stand overnight.

To the slurry was added 10 ml of water and the product was collected by filtration and dried overnight in a drying oven to give 7.5 g (83.6%) of N-cyclobutylmethyl-14-hydroxydihydronormorphine hydrobromide, m.p. 275°–276°.

EXAMPLE 3

Sodium Bromide As Demethylation Rate Enhancer

To a 100 ml round bottom flask equipped with a condenser and nitrogen purge was charged N-cyclobutylmethyl-14-hydroxydihydronorcodeine (7.6 g, 20 mmoles), sodium bromide (2.1 g, 20 mmoles). 48% aqueous hydrobromic acid (16.6 g, 100 mmoles) and 3.4 g of deionized water. The resulting mixture was heated to 103° and refluxed at 103±2° for 6 hours, during which time the initial tan solution turned to a lavender slurry. Thin layer chromatography indicated approximately 97–98% conversion. The resulting slurry was cooled to 25° and was allowed to stand overnight.

To the slurry was added 10 ml of water and the product was collected by filtration and dried overnight in a drying oven to give 7.7 g (85.9%) of N-cyclobutylmethyl-14-hydroxydihydronormorphine hydrobromide, m.p. 281°–282°.

EXAMPLE 4

Potassium Bromide As Demethylation Rate Enhancer

To a 100 ml round bottom flask equipped with a condenser and nitrogen purge was charged N-cyclobutylmethyl-14-hydroxydihydronorcodeine (7.6 g, 20 mmoles), potassium bromide (2.4 g, 20 mmoles), 48% aqueous hydrobromic acid (16.6 g, 100 mmoles) and 3.1 of deionized water.

The resulting mixture was heated to 103° and then refluxed at 103±2° for 6 hours, during which time the tan solution became a lavender slurry. Thin layer chromatography indicated approximately 97–98% conversion. The resulting slurry was cooled to 25° and was allowed to stand overnight.

To the slurry was added 10 ml of water and the product was collected by filtration and dried overnight in a drying oven to give 7.7 g (85.9%) of N-cyclobutylmethyl-14-hydroxydihydronormorphine hydrobromide, m.p. 283°–284°.

Following the procedures of Examples 1–4, rate enhancements for the demethylation of N-cyclobutylmethyl-14-hydroxydihydronorcodeine in aqueous hydrobromic acid were established for a variety of inorganic bromides and boric acid as set forth in the following Table I.

TABLE I

| Inorganic Bromides or Boric Acid/ Aqueous Hydrogen Bromide Demethylations | | |
|---|---|---|
| Example No. | Salt | Relative Rate |
| Control | — | 1 |
| 1 | MgBr$_2$ | ~4 |
| 2 | LiBr | ~5 |
| 3 | NaBr | ~4 |
| 4 | KBr | ~4 |
| 5 | AlBr$_3$ | ~4 |
| 6 | CaBr$_2$ | ~4 |
| 7 | MnBr$_2$ | ~3 |
| 8 | NiBr$_2$ | ~3 |
| 9 | Boric acid | ~5 |
| Comparative Ex. | SnBr$_2$ | ~2 |
| Comparative Ex. | ZnBr$_2$ | ~1 |
| Comparative Ex. | CeBr$_3$ | ~1 |

Following similar procedures, rate enhancements were also established for the demethylation reaction employing a variety of inorganic salts in aqueous hydrogen chloride. The results of the magnesium chloride/hydrogen chloride demethylation and several hybrid system demethylations are summarized on pages 4 and 5.

What is claimed is:

1. In the process of dealkylating an opioid ether by contacting the ether with an aqueous acid selected from HBr or HCl, the improvement comprising: contacting the ether with the aqueous acid containing at least one equivalent weight, based on the ether, of boric acid or a bromide or chloride salt of a metal selected from Li, Na, K, Al, Mg, and Ca.

2. The process of claim 1 wherein the contacting is conducted at the reflux temperature of the resulting mixture.

3. The process of claim 2 wherein the aqueous acid is hydrobromic acid.

4. The process of claim 3 wherein the hydrobromic acid contains at least one equivalent weight of boric acid or a halide salt of Li, Na, K, Mg, or Ca.

5. The process of claim 3 wherein the hydrobromic acid contains at least one equivalent weight of MgBr$_2$.

6. The process of claim 1 wherein the ether is a methyl ether of an opioid.

7. The process of claim 1 wherein the ether is an N-substituted 14-hydroxydihydronorcodeine.

8. The process of claim 5 wherein the ether is a methyl ether of an opioid.

9. The process of claim 5 wherein the ether is an N-substituted 14-hydroxydihydronorcodeine.

10. The process of claim 9 wherein the N-substituent is cyclobutylmethyl.

* * * * *